US005995939A

United States Patent [19]
Berman et al.

[11] Patent Number: 5,995,939
[45] Date of Patent: Nov. 30, 1999

[54] AUTOMATED NETWORKED SERVICE REQUEST AND FULFILLMENT SYSTEM AND METHOD

[75] Inventors: Keith Berman, Westlake Village; Sima Mishail, Woodland Hills; William Tappin, Agoura Hills; Barbara Asbell, Ventura; Tom V. Nguyen, Canoga Park, all of Calif.

[73] Assignee: Cymedix Lynx Corporation, Englewood, Colo.

[21] Appl. No.: 08/950,328

[22] Filed: Oct. 14, 1997

Related U.S. Application Data

[60] Provisional application No. 60/028,397, Oct. 15, 1996.

[51] Int. Cl.$^6$ .................................................. G06F 17/60
[52] U.S. Cl. ...................... 705/3; 705/2; 705/4; 707/104
[58] Field of Search .................................. 705/1, 2, 3, 26, 705/27, 35; 707/1, 2, 3, 8, 9, 10, 100, 101, 102, 104; 395/186, 187.01, 188.01, 200.3, 200.33, 200.42, 200.43, 200.47

[56] References Cited

U.S. PATENT DOCUMENTS

| | | | |
|---|---|---|---|
| 4,799,156 | 1/1989 | Shavit | 705/26 |
| 4,951,196 | 8/1990 | Jackson | 705/37 |
| 5,136,291 | 8/1992 | Teague | 341/83 |
| 5,557,780 | 9/1996 | Edwards et al. | 395/500.48 |
| 5,579,393 | 11/1996 | Conner et al. | 380/25 |
| 5,608,874 | 3/1997 | Ogawa et al. | 395/200.76 |
| 5,664,109 | 9/1997 | Johnson et al. | 705/2 |
| 5,758,126 | 5/1998 | Daniels et al. | 345/333 |
| 5,829,001 | 10/1998 | Li et al. | 707/10 |

OTHER PUBLICATIONS

Vaughan–Nichols; "The Great Communicator: Windows E–Mail Programs"; *Computer Shopper*; v13 n11; p. 520(7); Nov. 1993; DIALOG: File 275; Acc# 01621909.

"Access Healthnet Announces Agreement with Unilab to Provide Northern California Healthcare Agencies with Community Health Information Network"; *PR Newswire*; p. 1002LA017; Oct. 2, 1995; DIALOG: File 148; Acc# 08168454.

Bailes; "Eudora 3.0 is Powerful Yet Easy to Use"; *Info-World*; v18 n50; PIW6(1); Dec. 9, 1996; DIALOG: File 148, Acc# 09157585.

*Primary Examiner*—Stephen R. Tkacs
*Attorney, Agent, or Firm*—Koppel & Jacobs

[57] ABSTRACT

An automated networked service request and fulfillment system and method includes "client" computer systems in the offices of professionals such as doctors, and "sponsor" computers at the sites of service providers such as test labs or insurance companies, interconnected with a mail server system that exchanges e-mail messages via the Internet or a similar network. "Service requests", such as ordering a medical test or requesting authorization for a particular procedure, are prepared using a client system and automatically e-mailed to the sponsor system of an appropriate service provider. The request is fulfilled and the results e-mailed back to the requesting client system using the mail server system. Confidentiality is insured by encrypting all e-mail messages. The system includes a "universal interface" component which automates the process of converting data records found in existing databases into the data record format required by the new system.

21 Claims, 6 Drawing Sheets

AUTOMATED NETWORKED SERVICE REQUEST AND FULFILLMENT SYSTEM AND METHOD

This application is a continuation-in-part of Provisional Application No. 60/028,397, filed Oct. 15, 1996.

BACKGROUND OF THE INVENTION

1. Field of the Invention

This invention relates to the field of automated service request and fulfillment systems, particularly systems in which requests are made and fulfilled over a computer network.

2. Description of the Related Art

The health care industry and its endlessly spiraling costs are subjects of great concern at present, with new methods of managing medically-related information introduced regularly. A labor intensive approach has traditionally been taken to manage such information: a doctor orders a medical procedure on a multi-ply form, and a copy is delivered to a medical center by the patient, a courier, or via facsimile or mail. The results are returned to the doctor in similar fashion, recorded on paperwork which is physically carried back to the ordering doctor's office. Verifying a patient's medical insurance status traditionally requires that personnel working in a doctor's office or health care facility consult the latest revision of an insurer's printed "eligibility" list, or attempt to learn the status via telephone.

In the "managed health care" operating environment favored by health maintenance organizations (HMOs), member doctors typically must request and receive "authorization" from a patient's HMO prior to performing a particular medical procedure. The request for authorization, and its subsequent approval or denial, are commonly handled with an exchange of paperwork, via the mails. Similarly, permission to refer a patient to another doctor is usually requested and received via mailed or hand-delivered paperwork.

Many modern offices have attempted to improve their efficiency by introducing computers. A myriad of "complete medical office management" software products are in use which keep track of patient information and medical histories, billing and insurance information, etc. These products generally place such information into "data records" which are stored in one or more databases within a personal computer. The "format" of the information in a data record, i.e., the precise arrangement of text, data, and control characters which make up the record, is unique to most of the products in the market, as is the way in which the data records are arranged into a database. When an office adopts a new management system, a transfer of the stored information from the existing database to a new database is necessitated. However, because of the differences in the data record and database formats of the old and new products, such a transfer is typically accomplished by manually re-entering data into the new database one record at a time.

Some offices have linked their computer systems to various insurance providers via costly, proprietary computer networks, for purposes of determining insurance eligibility, for example. However, as with the office management software products, most of the existing network systems are unique, with each system having its own set of system requirements, operating procedures, and communications protocols. Confidentiality is also a serious concern when using a network, and while some network-based systems do encrypt the data sent over the network, the quality of the various encryption schemes and the procedures associated with them tend to vary widely. Also, many of these networks are arranged so that their user interface screens must be downloaded into the office computer over the network, which often results in long delays and poor responsiveness for the user due to the large amount of data that must be transferred over the network.

Similar problems and attempted solutions are found in other professional fields. For example, a brokerage may store investor identification and portfolio information in a database of some sort. The brokerage may need to communicate with a variety of off-site service providers, such as financial exchanges, quotation services, etc. As in the medical field, many software products and proprietary networks have been introduced to improve the management of financial information, but the vast technical differences which exist between competing products tends to also provide a host of incompatibility, upgrading and training problems.

SUMMARY OF THE INVENTION

A system and a method are presented for making and fulfilling service requests between two or more remote sites over the Internet or a similar computer network, which overcome many of the problems noted above.

The novel system uses a client-server electronic mail (e-mail) architecture. A "client" computer system is located in the office of a professional such as a doctor, a "sponsor" (server) computer system is located at the site of a service provider, such as a testing lab, hospital, or insurance company, and a network-based mail server system serves as an interface between the two.

A client makes "service requests" by entering information on an appropriate request screen generated on the client system's display by resident software. Typical service requests might include the ordering of a blood test for a particular patient, a request for authorization to perform a particular medical procedure, or a request for a quotation on a particular financial investment product. The client system formats a completed service request into a "service request message", which is e-mailed to the sponsor system of a service provider capable of providing the requested service using the mail server system. The sponsor system monitors its mailbox for service request messages, retrieves those found, and submits them to the service provider for processing.

The service provider processes the service request message and the results are formatted into a "fulfilled service request" message, which the sponsor system e-mails back to the requesting client using the mail server system. The client system monitors its mailbox for fulfilled service request messages, retrieves those found, and presents them to the requester on demand.

A complete system per the present invention typically includes hundreds of client systems and dozens of sponsor systems, with every system able to communicate with every other system via the Internet. For example, client systems might be located in the respective offices of all the member doctors of an HMO, with sponsor systems located at a number of facilities which provide various services to the HMO.

To insure the confidentiality of sensitive data, both the service request and the fulfilled service request messages are preferably encrypted. Further privacy is achieved by separating each encrypted message into two messages: a "public" data message, which might include patient identification information, and a "private" data message, containing the results of the patient's blood test, for example.

The mail server system can be any network-based system intended to enable the exchange of e-mail messages between computers at remote sites. An e-mail provider operating on the Internet is a primary example; a corporation's proprietary intranet between facilities is another.

The present system requires that a database of information, such as the identities of a roster of patients, be built up on the client system. Many professional offices have existing databases containing this information. The invention includes a "universal interface" software component which automates the process of converting this information from its existing form into the format required by the new system.

Further features and advantages of the invention will be apparent to those skilled in the art from the following detailed description, taken together with the accompanying drawings.

DETAILED DESCRIPTION OF THE INVENTION

Figure 1:
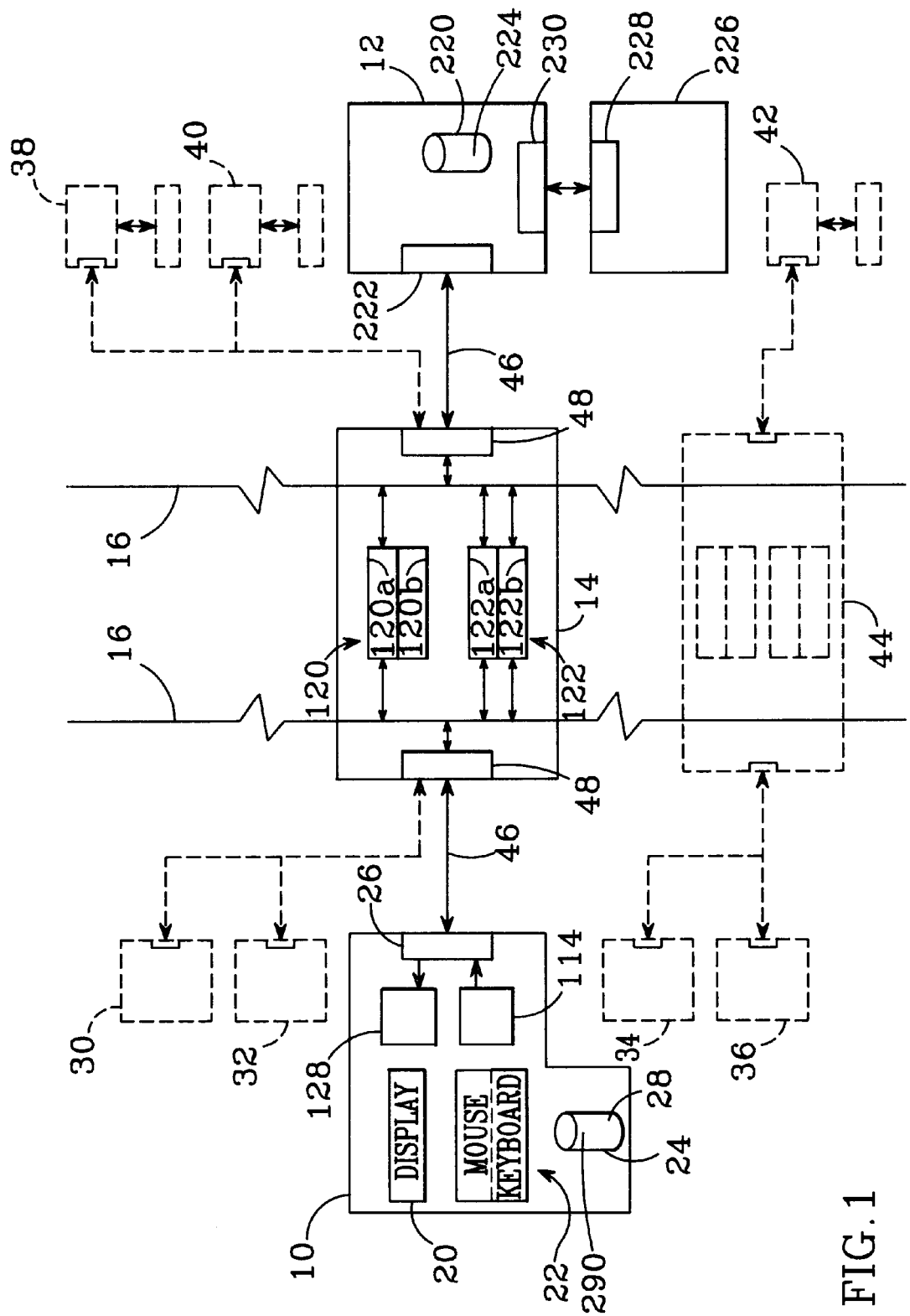
FIG. 1 is a block diagram of an automated service request and fulfillment system per the present invention.

An automated networked service request and fulfillment system is shown in FIG. 1. The system includes a client system 10, a sponsor system 12, and a mail server system 14 which employs a computer network 16. Service requests are made by entering data into a screen displayed on the client system, which formats the entered data into "service request messages" which are electronically mailed ("e-mailed") to a sponsor system or another client system via the computer network. The recipient of the service request message processes the request, formats the results into a "fulfilled service request message", and e-mails the fulfilled service request message back to the client system that made the request.

The client system 10 is preferably a personal computer (PC) which includes a display device 20 such as a CRT or laptop screen, data entry devices 22 such as a mouse and keyboard, and a directly accessible "local" data storage medium 24, such as a hard disc drive. Client system 10 uses the "WINDOWS" operating system, version 3.1 or greater, or Windows NT, version 3.5 or greater, made by Microsoft Corp. of Redmond, Wash. The client system also includes a network communication interface 26, such as a conventional modem.

The present invention includes software 28 stored on data storage medium 24. Client system 10 executes the instructions making up software 28 to enable a user to create and send service request messages to other, off-site computers such as sponsor system 12, and to receive fulfilled service request messages back from those off-site systems. Software 28 is referred to herein as the "client software".

The invention is particularly well-suited for use in the health care industry. In this context, the client system 10 is typically in a doctor's office, and sponsor system 12 is, for example, at an insurance company, testing lab, or hospital. The kinds of service requests that might be prepared and e-mailed by personnel in the doctor's office include: an order for a specific blood test to be performed at a specific testing lab for a specific patient; a request that a particular medical procedure or referral be authorized by a particular insurance company for a particular patient; a request that a patient be admitted to a local hospital; a request that the eligibility of an individual patient for insurance coverage be verified. For these examples, a sponsor system 12 is located at the site of each of the service providers: at the testing lab, the insurance company, and the hospital. Upon receiving a service request message from client system 10, the service provider performs the requested service: the testing lab performs the requested blood test and produces the test results, the insurance company decides whether or not to provide authorization for a procedure or referral or looks up a patient's eligibility, or the hospital pre-admits the patient pending his arrival.

The service provider processes the service request by performing the requested service, and the results of the processing, consisting in the above examples of the test results, the authorization decision or eligibility status, or the pre-admission confirmation, are received by the sponsor system and formatted into a fulfilled service request message which is e-mailed back to the original requester.

Though designed and implemented with the health care industry in mind, the invention is not limited to this field. A system as presented herein, with which a client can request and receive specific services from remote providers over a computer network, also finds use, for example, in the financial industry or legal field. A brokerage house could employ a client system, with a financial exchange and/or quotation service as service providers. Requests to buy or sell a certain security on the exchange, or for the current price of a particular investment product, could be made over a computer network with a system as herein described, with a resulting transaction confirmation or price quotation returned to the requester over the network. Similarly, a legal practitioner might order service of process on a particular individual by a process-serving service, or arrange for a court stenographer to be present at a certain time and place, with request and confirmation messages sent over a computer network.

A practical automated networked service request and fulfillment system per the present invention includes many, perhaps hundreds or thousands, of client systems 10, 32, 34, 36, and a smaller number of sponsor systems 12, 38, 40, 42, with all client and sponsor systems linked by computer network 16. Each client and sponsor system linked to network 16 is able to send service request messages and receive fulfilled service request messages from any other system similarly linked.

Mail server system 14 is typically provided by a commercial Internet provider which offers e-mail services, such as America Online. However, mail server system 14 can also be a system that controls a corporate intranet. As implemented, the invention exchanges service request messages and fulfilled service request messages which have been formatted as standard Simple Mail Transfer Protocol (SMTP) e-mail messages, and the mail server system preferably follows this standard. The inventive concept is valid for other message formats, of course, but the invention as implemented would require modification to accommodate a non-SMTP format. While any number of different mail server systems 14, 44 may be employed, the overall system requires that all the mail server systems used by the various client and sponsor systems be able to exchange e-mail messages. This characteristic is found amongst the many different Internet service providers: because the providers are all connected together via the Internet, an e-mail message can be sent by an originator and received by an addressee even if they subscribe to different Internet providers.

The client system 10 is connected to the mail server system 14 using communication lines 46, which could be conventional phone lines or dedicated high-speed data lines, for example. The client system's network communication interface 26 must be compatible with the type of lines 46 used, and the mail server system must also employ an interface 48 capable of handling the data conveyed over lines 46. Once received by the mail server system 14, e-mail messages are conveyed to their addressee via computer network 16.

A service request is initiated by executing the instructions making up client software 28, which, as noted above, is stored on directly accessible data storage medium 24. Requiring the client software 28 to be directly accessible to the client system eliminates the slow response problems inherent in network systems which must transmit most or all of their user interface over the network.

Once client software 28 is executed, a user may select from a number of different service request screens, each designed to prompt the user to provide the information necessary to carry out the specific request. The e-mail addresses of the sponsor systems to which each type of request is to be sent are preferably previously stored into a database on data storage medium 24.

Figure 2:
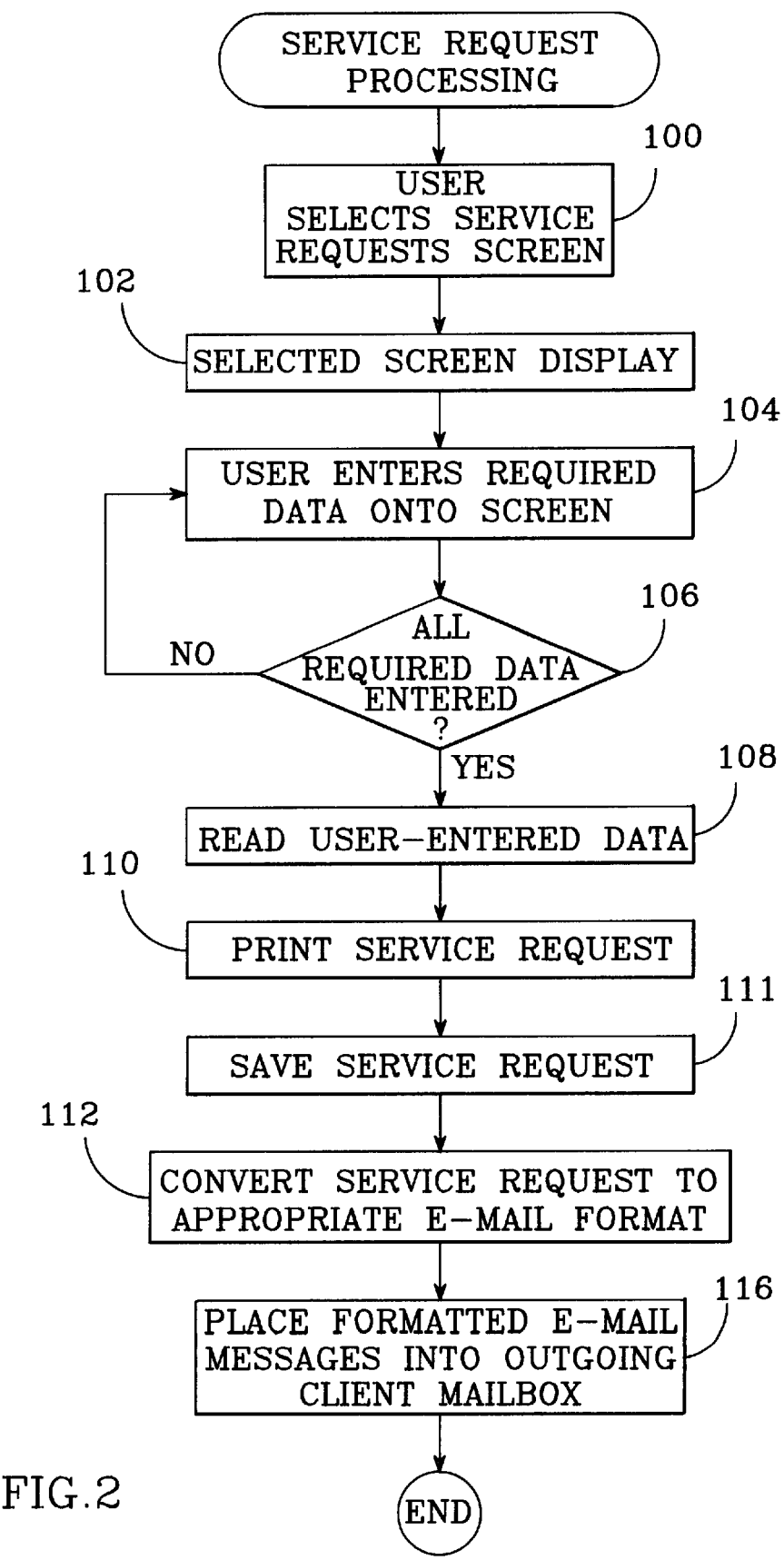
FIG. 2 is a flow diagram of the steps performed by a client system to prepare a service request message.

Once a service request screen is selected, instructions found in client software 28 carry out the sequence of steps shown in the flow diagram of FIG. 2. The user selects a screen in step 100, which is displayed on a display device 20 in step 102. The selected screen typically includes blank lines and spaces into which data is to be entered with data entry devices 22 (step 104). For example, the screen might display "NAME:_____", and the user is to type in the appropriate name. Other data may be entered with a mouse, by selecting a particular entry in a list by clicking on it, for example. The user is not permitted to continue until all necessary data has been entered, which is tested at step 106. If all required data has been entered, the entries are read by the software at step 108, and a hard copy of the service request is automatically printed out at step 110.

At step 111, the completed service request is preferably saved into a file which the user is prompted to specify. By saving the service requests, a user may, at his option, reprint the service request at any time in the future.

The software 28 converts the service request into a service request e-mail message at step 112, formatting the message as required by the network over which the message is to be sent. At the present time, e-mail messages sent over the Internet must be in standard SMTP format.

In addition to the SMTP message format, the content of the e-mail messages exchanged across the system, whether sent by a client or a sponsor system, preferably adhere to a particular format as well. The message content standard with which the present system has been implemented is the "HEALTH LEVEL 7" standard developed by Health Level 7 Corp. of Ann Arbor, Mich. This standard, specifically designed for the exchange of medically sensitive information over a computer network, does the following to a service request or fulfilled service request message sent over a computer network: 1) splits the message into two e-mail messages: a "public" data message, which might include patient identification information, for example, and a "private" data message, containing the results of the patient's blood test, for example; 2) encrypts both private and public messages using the Pretty Good Privacy (PGP) encryption scheme which is publicly available on the Internet, using different private and public keys for the two messages; and 3) compresses the messages. The Health Level 7 standard also decompresses, decrypts and reassembles messages which have been received by the proper addressee. It is not essential that the present invention be implemented with this standard, but some means of security should be employed to insure the confidentiality of the information conveyed over the network.

Thus, at step 112, the service request message is preferably converted into a public message and a private message, both of which are encrytped, compressed, and formatted in compliance with the SMTP message format.

The formatted messages are placed into an outgoing client mailbox 114 (identified in FIG. 1) at step 116, which consists of an area of the client system's local data storage 24 designated for this purpose.

Referring back to FIG. 1, electronic mailboxes are established in the various mail server systems 14, 44 utilized by the clients and sponsors. Electronic "remote sponsor mailboxes" 120 are maintained by the mail server system, to which the service request messages in outgoing client mailbox 114 are sent (as described below). Each of the remote sponsor mailboxes 120 is associated with a respective service provider. Because outgoing service request messages are divided into separate private and public messages, remote sponsor mailbox 120 is divided into two sections: a private data mailbox 120*a* and a public data mailbox 120*b*, with each section having its own e-mail address.

A "remote client mailbox" 122 is also maintained by the mail server system, to which fulfilled service request messages are sent (as described below). Remote client mailbox 122 is also preferably divided into a private data mailbox 122*a* and a public data mailbox 122*b*, each with its own e-mail address.

Figure 3:
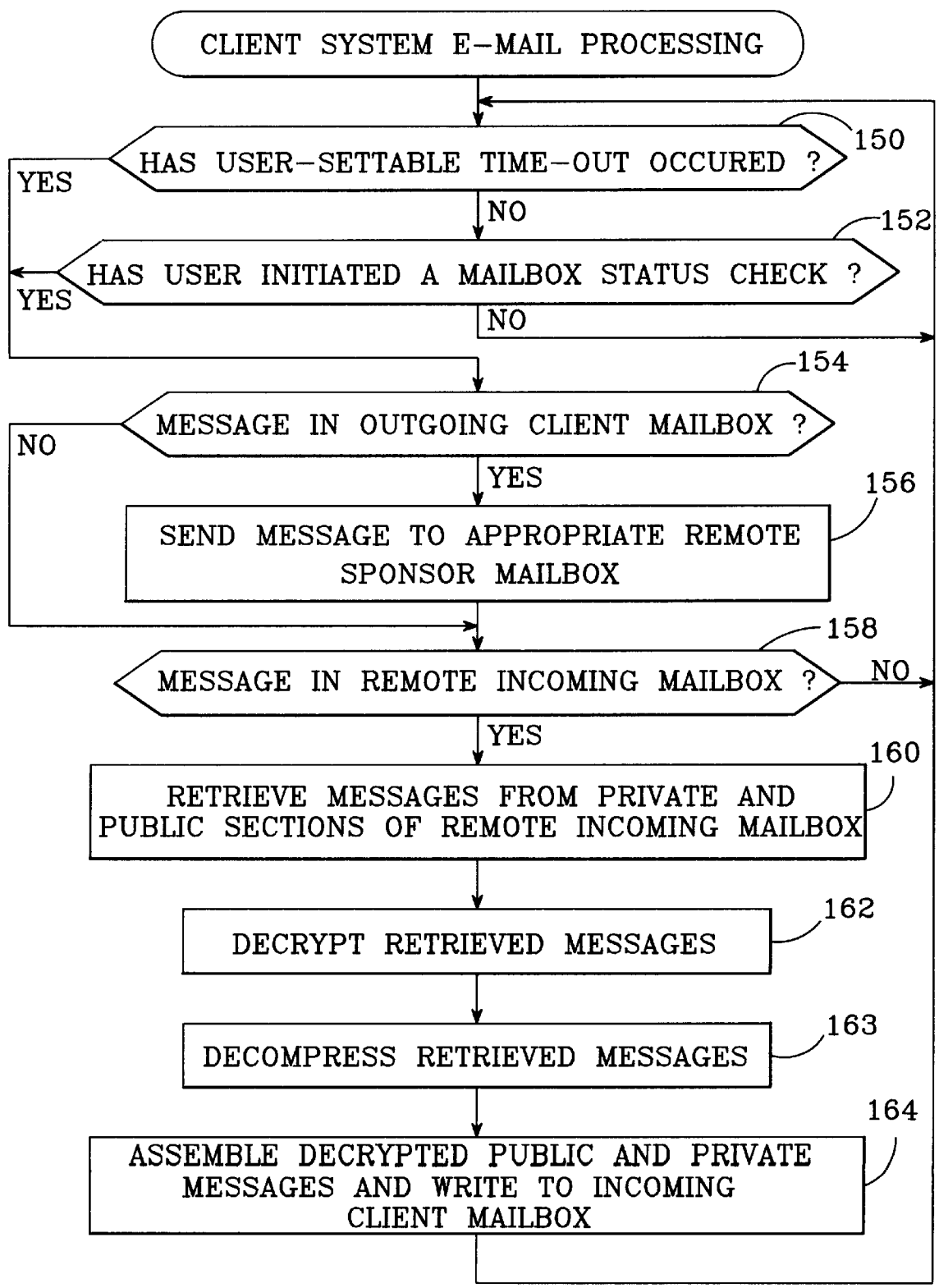
FIG. 3 is a flow diagram of the steps performed by a client system to send outgoing and retrieve incoming e-mail messages.

The client system 10 also includes an incoming client mailbox 128, into which fulfilled service request messages are put when retrieved from remote client mailbox 122. The client software 28 controls the transfer of e-mail messages out of and into the outgoing and incoming mailboxes 114 and 128, respectively, with the process steps used to control these transfers shown in the flow diagram of FIG. 3.

The presence of a message to be sent in outgoing client mailbox 114 is detected in one of two ways. In step 150, a user-settable timer is monitored to see whether it has timed-out. Alternatively, a check of mailbox 114 can be initiated by the user, as shown in step 152. If either event has occurred, the outgoing client mailbox 114 is checked for messages at step 154.

If a message is found in step 154, the message is sent to the e-mail address associated with the appropriate remote sponsor mailbox at step 156. The e-mail addresses of all sponsors in the system are typically in a database stored on data storage medium 24, and the software 28 automatically retrieves and attaches the appropriate address to the outgoing service request message based on the type of request being made.

After all outgoing messages have been e-mailed, the remote client mailbox 122 is checked for fulfilled service request messages at step 158. If any are found, the private data message and public data message components of each fulfilled service request are retrieved at step 160.

The private and public data messages are decrypted at step 162, decompressed at step 163, and then reassembled into a fulfilled service request message and written to incoming client mailbox 128 at step 164. The program flow then returns to step 150. The continuously-looping sequence shown in FIG. 3 preferably runs in the background.

In practice, a typical time-out period at step 150 would be about 30 minutes, to insure that newly-created service request messages are promptly sent and that fulfilled service request messages recently sent by a sponsor system are promptly retrieved.

Figure 4:
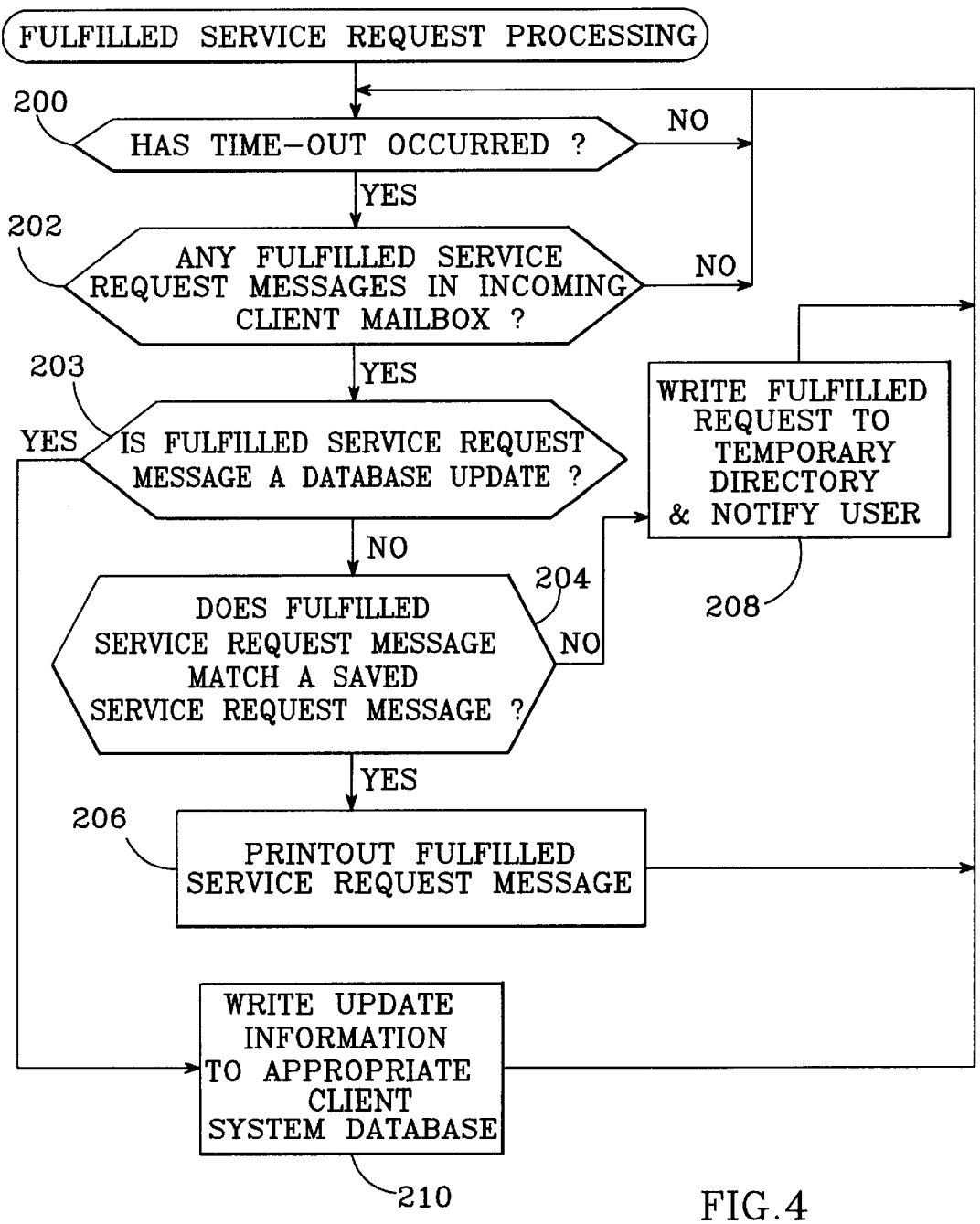
FIG. 4 is a flow diagram of the steps performed by a client system to process retrieved e-mail messages.

Fulfilled service request messages written to incoming client mailbox 128 are processed in accordance with the steps shown in the flow diagram of FIG. 4. The incoming client mailbox is checked for fulfilled service request messages when a time-out period, preferably about 30 seconds, expires, as shown in steps 200 and 202.

As the system is implemented, a fulfilled service request message found in the incoming client mailbox takes one of two forms: it can either be received in response to a service request message previously e-mailed from the client system, or it can be sent by a sponsor system as a "database update". Database updates are sent by service providers such as insurance companies, to update information such as price schedules, doctor referral rosters, or diagnosis rosters stored in databases on the client system. A message adhering to Health Level 7 format distinguishes between these two message types based on the message's "header". At step 203, client software 28 determines which type of message is present.

If client software 28 determines that the message is a fulfilled service request message, an attempt is made at step 204 to match the fulfilled request with the service requests saved at step 111 of FIG. 2. If a match is found, the fulfilled service request message is automatically printed at step 206. If not, the fulfilled service request message is written to a temporary file and the user notified (at step 208). The program flow then returns to step 200.

If client software 28 determines that the message is a database update, processing continues at step 210, where the update information is written into the proper database on the client system, and program flow then returns to step 200. The continuously-looping sequence shown in FIG. 4 preferably runs in the background.

Referring back to FIG. 1, sponsor systems 12, 38, 40, 42 also use the "WINDOWS" operating system, version 3.1 or greater, or Windows NT version 3.5 or greater. The sponsor systems each include a directly accessible data storage medium 220 and a network communication interface 222. The primary function of the sponsor systems is to retrieve service request messages sent to them from any of client systems 10, 30, 32, 34, 36 and to e-mail fulfilled service request messages back to the requesting client systems. Software 224 residing on storage medium 220 controls the receiving and sending of the requests, and is referred herein as the "sponsor software".

The sponsor system 12 will usually be connected to a "legacy system" 226. The legacy system typically includes a "legacy communication interface" 228 with which it connects to a sponsor system 12. When a legacy and sponsor system are configured in this way, the sponsor system 12 includes a "sponsor communication interface" 230. Data is bidirectionally exchanged between the two systems via their respective communication interfaces 228 and 230.

The legacy system 226 is typically the computer system a service provider has traditionally used prior to procuring the present invention. The service provider's personnel interact with the legacy system, with the sponsor system generally operating automatically and without intervention. Service request messages received by the sponsor system are automatically transferred to the legacy system for processing by the service provider. The necessary work is performed: a patient's blood test is run, a decision is made regarding the authorization of a requested medical procedure, etc., and the results of the work are entered into the legacy system. The sponsor system 12 automatically retrieves results from the legacy system 226, assembles a fulfilled service request message, and e-mails the fulfilled service request message back to the requesting client system 10.

It is not essential that the legacy system 226 and sponsor system 12 be separate systems: a single system of sufficient processing and storage capacity could serve as both systems, with the capacities needed dependent on the amount of incoming service request messages. However, because a service provider's legacy system is generally not designed to handle a high volume of Internet e-mail, a separate sponsor system is recommended.

The sponsor system 12 must submit service request messages to and receive results from a legacy system 226. Because different legacy systems handle these data exchanges differently, sponsor software 224 must be customized for the particular legacy system 226 being used by a particular service provider.

Figure 5:
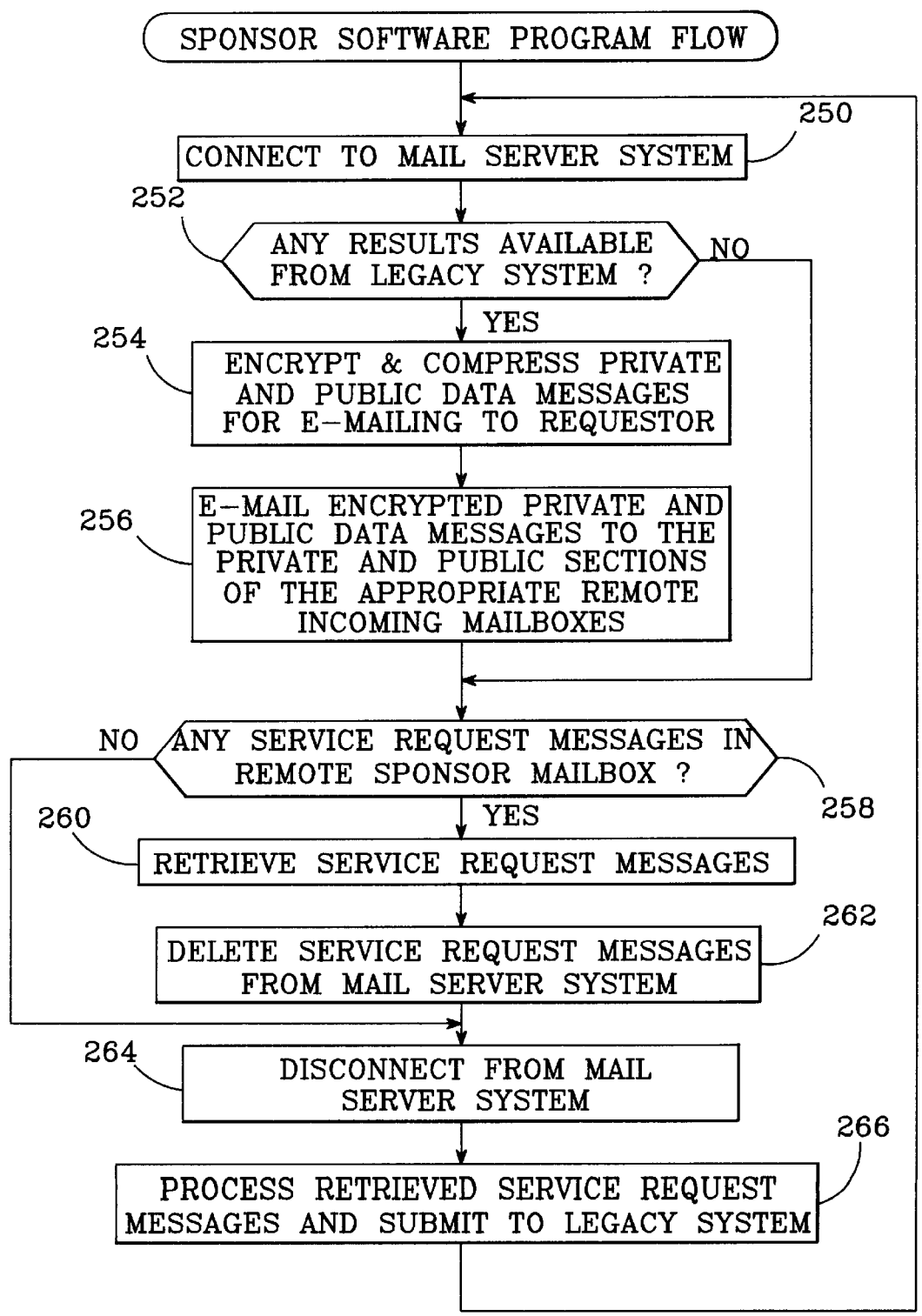
FIG. 5 is a flow diagram of the steps performed by a sponsor system to send outgoing and retrieve incoming e-mail messages.

The sequence of instructions followed by sponsor software 224 is shown in the flow diagram of FIG. 5. The sponsor system connects to the mail server system via its network communication interface 222 at step 250. If any results have been received from the legacy system (step 252), or if any database updates are to be sent, they are formatted into fulfilled service request messages at step 254. If the preferred Health Level 7 formatting is used, the fulfilled service request is divided into encrypted and compressed private and public data messages. At step 256, the private and public messages are e-mailed to the private and public sections, respectively, of the appropriate remote client mailboxes.

The system next proceeds to step 258, or jumps to step 258 directly if there were no results available at step 252, where the remote sponsor mailbox is checked for service request messages. If there are, the requests are retrieved into the sponsor system at step 260, and then deleted from the mail server system at step 262. The sponsor system is disconnected from the mail server system at step 264.

At step 266, service request messages retrieved at step 260 are processed and submitted to the legacy system. The sequence then cycles back to step 250.

The automated networked service request and fulfillment system described herein also includes a "universal interface" software component 290, typically stored on the client system's data storage medium 24 (identified in FIG. 1), which provides a solution to the problems encountered as a result of the myriad of database record formats presently in use in professional offices. In the past, converting these existing, "legacy" database records into the record and database format used by a new office management software package required hours of manual data re-entering. The universal interface program provides an automated method of importing the legacy data records, converting them into the record format used and needed by the client software 28, and storing the converted records into a new database. This process normally need only be performed once, when the automated networked service request and fulfillment system is first incorporated into an office. Once all the legacy records have been converted and stored into a new database, all new records are entered directly into the new database.

Figure 6:
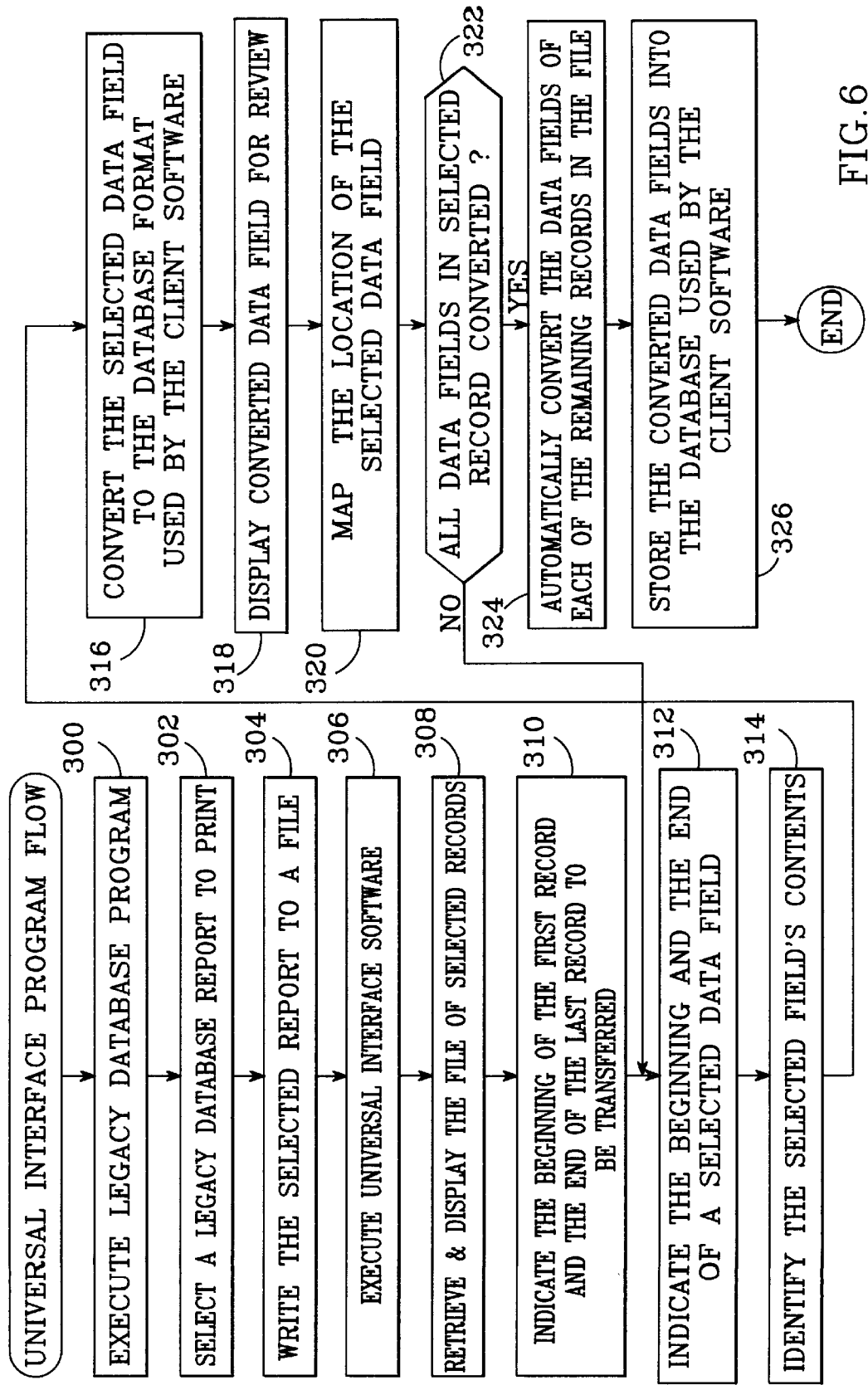
FIG. 6 is a flow diagram of the steps performed by a universal interface component of the present invention to convert legacy database information into the data record format used by a client system.

A flow diagram of the steps performed by the universal interface software is shown in FIG. 6. To transfer the data records stored in a first format in a legacy database into data records stored in the format and database used by client software 28, a user first executes the application program associated with the legacy database at step 300. Although there are many different database application programs in use, which use many different formats, one function common to nearly all such database programs is the ability to print out reports, such as a patient roster or a list of insurance providers. As a means of accessing a group of legacy data records, the user selects one of these reports to be printed at step 302. At step 304, the software 290 causes the report, which includes the database records to be transferred, to be written to a file rather than printed.

At step 306, the universal interface software 290 is executed on the system to which the legacy database records are to be transferred, which is typically the client system 10. At step 308, the file written at step 304 is retrieved by the software 290 and the contents displayed on display device 20. As displayed, the file is likely to include a header and a footer, with a number of data records between the header and footer. Each data record typically includes printer control characters, data labels and delimiters. Each record will also include "data fields", which contain information such as a patient's name, ID number, birth date, sex, etc. It is the data fields from each data record in the file which are to be transferred into the new database.

At step 310, the user indicates the beginning of the first record to be transferred and the end of the last record to be transferred, using the mouse, for example, to define for software 290 the area in which the data of interest is confined.

At step 312, the user selects a data field to convert from within a selected data record, preferably the first data field of the first data record, and indicates the beginning and end of the selected field. As implemented, this is done by "highlighting" the data field by dragging the mouse cursor across it. At step 314, the contents of the highlighted field are identified. A list of possible identifiers is presented, including labels such as "Patient ID", "Name", "Date Of Birth", and "Sex", and the user selects the entry on the list that describes the highlighted field.

Now that the selected data field's text has been highlighted and identified with a particular label, software 290 converts the highlighted field into the database format used by client software 28 at step 316, which can be any of a number of user-determined formats including the Health Level 7 database format. The converted data field is displayed for review at step 318, to verify that the field was correctly converted.

At step 320, software 290 "maps" the location of the data field just converted, by noting its position in relation to the beginning of the selected record, and the characters which precede and follow the field, for example.

If there are more data fields to be converted in the selected record, the software 290 branches (at step 322) back to step 312 and another data field is highlighted. Steps 312, 314, 316, 318 and 320 are repeated until all the data fields of interest in the selected record have been converted, displayed, reviewed and mapped. If there are data fields in the selected record which are not needed in the new database, they are simply ignored during this sequence of steps.

When all data fields of interest in the selected record have been processed as discussed above, the program flow moves to step 324. Here, the software 290 automatically converts the data fields of interest in all the remaining data records in the file to the format required by the client software database. The start and end of the data records in the file were defined at step 310, and the description and location of each data field within a record were identified and mapped at steps 314 and 320, respectively. This information is used by software 290 to properly locate and convert the data fields of interest in each of the remaining data records, without user intervention. At step 326, the converted data fields from each of the file's data records are stored into the database used by client software 28.

The file created at step 304 may contain hundreds or thousands of data records. Because all but one record are converted automatically, a significant time and cost savings results from using the universal interface software 290 to establish the new database needed by client software 28.

The sequence of steps shown in FIG. 6 is repeated for each of the legacy database reports which contain data needed by client software 28. The legacy database's "patient roster" and "insurance providers" reports are the reports most typically run through the universal interface for conversion.

The universal interface software 290 can be used effectively with virtually any legacy database. Because the user defines the location of the data fields for the software 290, the method works regardless of the particular spacing and delimiters employed by the legacy database.

Client software 28, sponsor software 224, and universal interface software 290 are not limited to any particular programming language or software product. As presently implemented, Microsoft's "Visual C++" is used for all program logic, and Sybase's "SQL Anywhere" is used to provide both client and sponsor databases. Microsoft Corp. is in Redmond, Wash., and Sybase Corp. is in Emeryville, Calif.

While particular embodiments of the invention have been shown and described, numerous variations and alternate embodiments will occur to those skilled in the art. Accordingly, it is intended that the invention be limited only in terms of the appended claims.

We claim:

1. An automated service request and fulfillment system for use over a computer network, comprising:

a client system which includes a display device, a data entry device, a data storage medium and a network communication interface, said client system programmed to:

retrieve a service request screen stored on said data storage medium and display said screen on said display device, accept data entered onto said service request screen with said data entry device and generate a service request message which includes said data, electronically mail (e-mail) said service request message through said client system's network communication interface and over a computer network to a remote sponsor mailbox, and retrieve fulfilled service request messages from a remote client mailbox over a computer network and through said client system's network communication interface, and a sponsor system which includes a network communication interface, said sponsor system programmed to:

retrieve service request messages from said remote sponsor mailbox over a computer network and through said sponsor system's network communication interface, receive the results of processed service request messages and format them into fulfilled service request messages, and e-mail said fulfilled service request messages through said sponsor system's network communication interface and over a computer network to said remote client mailbox, wherein said remote client mailbox includes a public data mailbox and a private data mailbox, and said sponsor system divides a fulfilled service request message into public and private e-mail messages and separately e-mails said public and private e-mail messages into said public and private data mailboxes, respectively, over said computer network.

2. The system of claim 1, further comprising a mail server system connectable to said client system, said sponsor system and to a computer network, said mail server system arranged to maintain said remote client and sponsor mailboxes and to transfer messages between said mailboxes via said network.

3. The system of claim 1, wherein said sponsor system encrypts a fulfilled service request message when e-mailed to said remote client mailbox, and said client system decrypts said fulfilled service request message when retrieved from said remote client mailbox.

4. The system of claim 1, wherein said sponsor system compresses a fulfilled service request message when e-mailed to said remote client mailbox, and said client system decompresses said fulfilled service request message when retrieved from said remote client mailbox.

5. The system of claim 1, wherein said client system encrypts a service request message when e-mailed to said remote sponsor mailbox, and said sponsor system decrypts said service request message when retrieved from said remote sponsor mailbox.

6. The system of claim 1, wherein said client system compresses a service request message when e-mailed to said remote sponsor mailbox, and said sponsor system decompresses said service request message when retrieved from said remote sponsor mailbox.

7. The system of claim 1, further comprising a legacy system which is connectable to said sponsor system and programmed to receive a service request message from said sponsor system and to provide data to said sponsor system to be included in a fulfilled service request message.

8. The system of claim 1, further comprising a computer network connectable to said client and sponsor systems and arranged to convey service request messages and fulfilled service request messages between said remote client mailbox and said remote sponsor mailbox.

9. The system of claim 8, wherein said computer network is the Internet.

10. The system of claim 1, wherein said client system and said sponsor system e-mail service request messages and fulfilled service request messages, respectively, over said computer network as e-mail messages in Simple Mail Transfer Protocol (SMTP) format.

11. The system of claim 1, wherein said service request message comprises an order for a medical test to be performed on a patient.

12. The system of claim 1, wherein said service request message comprises a request for the authorization of a medical procedure by a patient's medical insurance company.

13. The system of claim 1, wherein said service request message comprises a request to verify the medical insurance coverage of a patient.

14. The system of claim 1, wherein said fulfilled service request message comprises the results of a medical test ordered with a corresponding service request message.

15. The system of claim 1, further comprising a plurality of additional client systems and a plurality of additional sponsor systems, arranged such that each of said client systems can send e-mail messages to and receive e-mail messages from each of said sponsor systems.

16. The system of claim 1, further comprising a plurality of additional client systems and a plurality of additional sponsor systems, arranged such that each of said client and sponsor systems can send e-mail messages to and receive e-mail messages from every other client and sponsor system.

17. The system of claim 1, wherein each of said service requests is fulfilled by a known one of a plurality of said sponsor systems, said client system further comprising a database of e-mail addresses for said sponsor systems and further programmed to automatically retrieve the e-mail address from said database for the sponsor system which fulfills the service request for which said retrieved service request screen is pre-formatted, and to use said retrieved e-mail address when e-mailing said service request message through said client system's network communication interface and over said computer network to said remote sponsor mailbox.

18. An automated service request and fulfillment system for use over a computer network, comprising:

a client system which includes a display device, a data entry device, a data storage medium and a network communication interface, said client system programmed to:

retrieve a service request screen stored on said data storage medium and display said screen on said display device, accept data entered onto said service request screen with said data entry device and generate a service request message which includes said data, electronically mail (e-mail) said service request message through said client system's network communication interface and over a computer network to a remote sponsor mailbox, and retrieve fulfilled service request messages from a remote client mailbox over a computer network and through said client system's network communication interface, and a sponsor system which includes a network communication interface, said sponsor system programmed to:

retrieve service request messages from said remote sponsor mailbox over a computer network and through said sponsor system's network communication interface, receive the results of processed service request messages and format them into fulfilled service request messages, and e-mail said fulfilled service request messages through said sponsor system's network communication interface and over a computer network to said remote client mailbox, wherein said remote sponsor mailbox includes a public data mailbox and a private data mailbox, and said client system divides a service request message into public and private e-mail messages and separately e-mails said public and private e-mail messages into said public and private data mailboxes, respectively, over said computer network.

19. The system of claim 1, wherein said sponsor system is further programmed to e-mail database updates and said client system is further programmed to receive said updates and to modify databases stored on said client system data storage medium to reflect said updates.

20. An automated service request and fulfillment system for use over a computer network, comprising:

a client system which includes a display device, a data entry device, a data storage medium and a network communication interface, said client system programmed to:
retrieve a service request screen stored on said data storage medium and display said screen on said display device,
accept data entered onto said service request screen with said data entry device and generate a service request message which includes said data,
electronically mail (e-mail) said service request message through said client system's network communication interface and over a computer network to a remote sponsor mailbox, and
retrieve fulfilled service request messages from a remote client mailbox over a computer network and through said client system's network communication interface, and a sponsor system which includes a network communication interface, said sponsor system programmed to:
retrieve service request messages from said remote sponsor mailbox over a computer network and through said sponsor system's network communication interface,
receive the results of processed service request messages and format them into fulfilled service request messages,
e-mail said fulfilled service request messages through said sponsor system's network communication interface and over a computer network to said remote client mailbox, and a new database stored on said client system's data storage medium, said client system further programmed to establish said new database by converting data records stored in a first format in an existing database to a second format in the new database, said converting accomplished by displaying the contents of said existing database, prompting a user to indicate the data to convert, converting said indicated data from said first to said second new format, and storing said converted data in said new database.

21. An automated service request system for use over a computer network, comprising:

a client system which includes a display device, a data entry device, a data storage medium and a network communication interface, said client system programmed to:
retrieve a service request screen stored on said data storage medium and display said screen on said display device,
accept data entered onto said service request screen with said data entry device and generate a service request message which includes said data,
electronically mail (e-mail) said service request message through said client system's network communication interface and over a computer network to a remote sponsor mailbox which is associated with a service provider capable of fulfilling said service request,
retrieve fulfilled service request messages from a remote client mailbox over a computer network and through said client system's network communication interface, and
a new database stored on said client system's data storage medium, said client system further programmed to establish said new database by converting data records stored in a first format in an existing database to a second format in the new database, said converting accomplished by displaying the contents of said existing database, prompting a user to indicate the data to convert, converting said indicated data from said first to said second new format, and storing said converted data in said new database.

* * * * *